US007256882B2

United States Patent
Gussman et al.

(10) Patent No.: US 7,256,882 B2
(45) Date of Patent: Aug. 14, 2007

(54) PHOTOMETER DEVICE AND METHOD

(75) Inventors: Robert A. Gussman, Winchester, NH (US); Kevin E. DeVoe, Waltham, MA (US)

(73) Assignee: BGI Instruments, Inc., Waltham, MA (US)

( * ) Notice: Subject to any disclaimer, the term of this patent is extended or adjusted under 35 U.S.C. 154(b) by 348 days.

(21) Appl. No.: 10/872,669

(22) Filed: Jun. 21, 2004

(65) Prior Publication Data

US 2005/0280820 A1    Dec. 22, 2005

(51) Int. Cl.
*G01J 1/00* (2006.01)
*G01N 15/06* (2006.01)
(52) U.S. Cl. .................. 356/213; 356/220; 250/573
(58) Field of Classification Search .......... 356/213, 356/220, 436, 437; 250/573
See application file for complete search history.

(56) References Cited

U.S. PATENT DOCUMENTS

| | | | | |
|---|---|---|---|---|
| 3,661,460 A | * | 5/1972 | Elking et al. | 356/36 |
| 3,869,208 A | * | 3/1975 | Lorenz | 356/336 |
| 4,368,119 A | * | 1/1983 | Wilson | 210/137 |
| 4,473,296 A | * | 9/1984 | Shofner et al. | 356/336 |

* cited by examiner

*Primary Examiner*—Roy M. Punnoose
(74) *Attorney, Agent, or Firm*—Iandioria & Teska

(57) ABSTRACT

A photometer device including an inlet passage for receiving a fluid such as an aerosol at a specified flow rate, an outlet passage separated from the inlet passage by a gap, and a radiation passage across the gap. The flow rate and the significant dimension of the inlet passage are set to produce a laminar flow of the aerosol. The gap and the significant dimension of the outlet passage are set to maintain a laminar flow of the aerosol across the gap to prevent contamination of the radiation passage.

8 Claims, 4 Drawing Sheets

PHOTOMETER DEVICE AND METHOD

FIELD OF THE INVENTION

This invention relates to particle monitoring and metering devices and, in one particular example, to a photometer and/or an adaptor for a photometer probe.

BACKGROUND OF THE INVENTION

In many industries, it is desirable to monitor airborne particles. Toxicoligists, for example, use a photometer to determine the concentration of particles administered to lab animals. Photometers are also used in the field to measure the concentration of airborne particles at a factory, for example. The concentration of dust in the air is also measured using a photometer.

A typical photometer is constructed to focus radiation (e.g., infrared radiation) through an aerosol passage. Optical components such as lenses collimate the radiation into a beam transverse to the flow of the aerosol containing the particles. Radiation scattered by the aerosol particles is detected by a detector such as a photodetector and the amount of scattered radiation detected is proportional to the concentration of the particles in the aerosol stream.

The particles, however, can contaminate and obscure the optical components of the photometer resulting in erroneous readings of the scattered radiation. As a result, the photometer must be recalibrated before each use which is a nuisance especially if the photometer is used often. Cleaning the optical lenses cannot generally be accomplished by the user.

Those skilled in the art have attempted to purge the lenses with air and have also attempted to maintain a positive pressure in the area of the lenses. Purge air at a low flow rate, however, is not effective at cleaning the lenses and purge air at a flow rate which might clean the lenses dilutes the aerosol stream resulting in erroneous particle concentration readings.

SUMMARY OF THE INVENTION

It is therefore an object of this invention to provide a photometer or a photometer adapter which prevents contamination of the radiation passage and the optical components associated therewith.

It is a further object of this invention to provide a method of preventing contamination of the photometer optical components without diluting the aerosol stream.

It is a further object of this invention to provide a photometer which does not require re-calibration after each use.

It is a further object of this invention to provide a photometer which does not need to be cleaned.

The subject invention results from the realization that if the aerosol stream through the radiation beam of a photometer is maintained as a laminar flow, the optical components associated with the radiation passage will remain free from contamination.

The subject invention, however, in other embodiments, need not achieve all these objectives and the claims hereof should not be limited to structures or methods capable of achieving these objectives.

This invention features a photometer device comprising an inlet passage for receiving a fluid such as an aerosol at a specified flow rate, an outlet passage separated from the inlet passage by a gap and a radiation passage across the gap. The flow rate and the significant dimension of the inlet passage are set to produce a laminar flow of the aerosol. Moreover, the gap and the significant dimension of the outlet passage are set to maintain a laminar flow of the aerosol across the gap to prevent contamination of the radiation passage.

In one preferred embodiment, the inlet passage significant dimension is less than the outlet passage significant dimension. In one example, the inlet passage is a round conduit and the significant dimension of the inlet passage is the inner diameter of the conduit. Also, the outlet passage is a round conduit and the significant dimension of the outlet passage is the inner diameter of the conduit.

In one embodiment, the photometer device is an adaptor for a photometer probe and includes a main block with the radiation passage therethrough, a first channel in the main block transverse to and in communication with the radiation passage for receiving an inlet tube defining the aerosol inlet passage. A second channel in the main block is transverse to and in communication with the radiation passage and receives an outlet tube defining the aerosol outlet passage. A filter unit may be coupled to the outlet tube.

In one example, a photometer probe adaptor in accordance with this invention features a main block with a radiation passage therethrough, an inlet conduit in the main block and having a distal end in fluid communication with the radiation passage, and an outlet conduit in the main block having a distal end in fluid communication with the radiation passage and spaced from the distal end of the inlet conduit by a gap within the radiation passage. The flow rate of the fluid and the significant dimension of the inlet conduit are configured or set to produce a laminar flow of the fluid. The significant dimension of the outlet conduit is also configured and the gap is set to maintain a laminar flow across the gap to prevent contamination of the radiation passage.

A method of preventing contamination of optical components in a device such as a photometer in accordance with this invention includes defining a gap between an inlet passage and an outlet passage, setting the flow rate of the fluid within the inlet passage, across the gap, and in the outlet passage, configuring the significant dimension of the inlet passage to provide a laminar flow of the fluid at the set flow rate, and configuring the significant dimension of the outlet passage and adjusting the gap to maintain the laminar flow of the fluid across the gap. Preferably, the significant dimension of the inlet passage is less than the significant dimension of the outlet passage.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Figure 1:
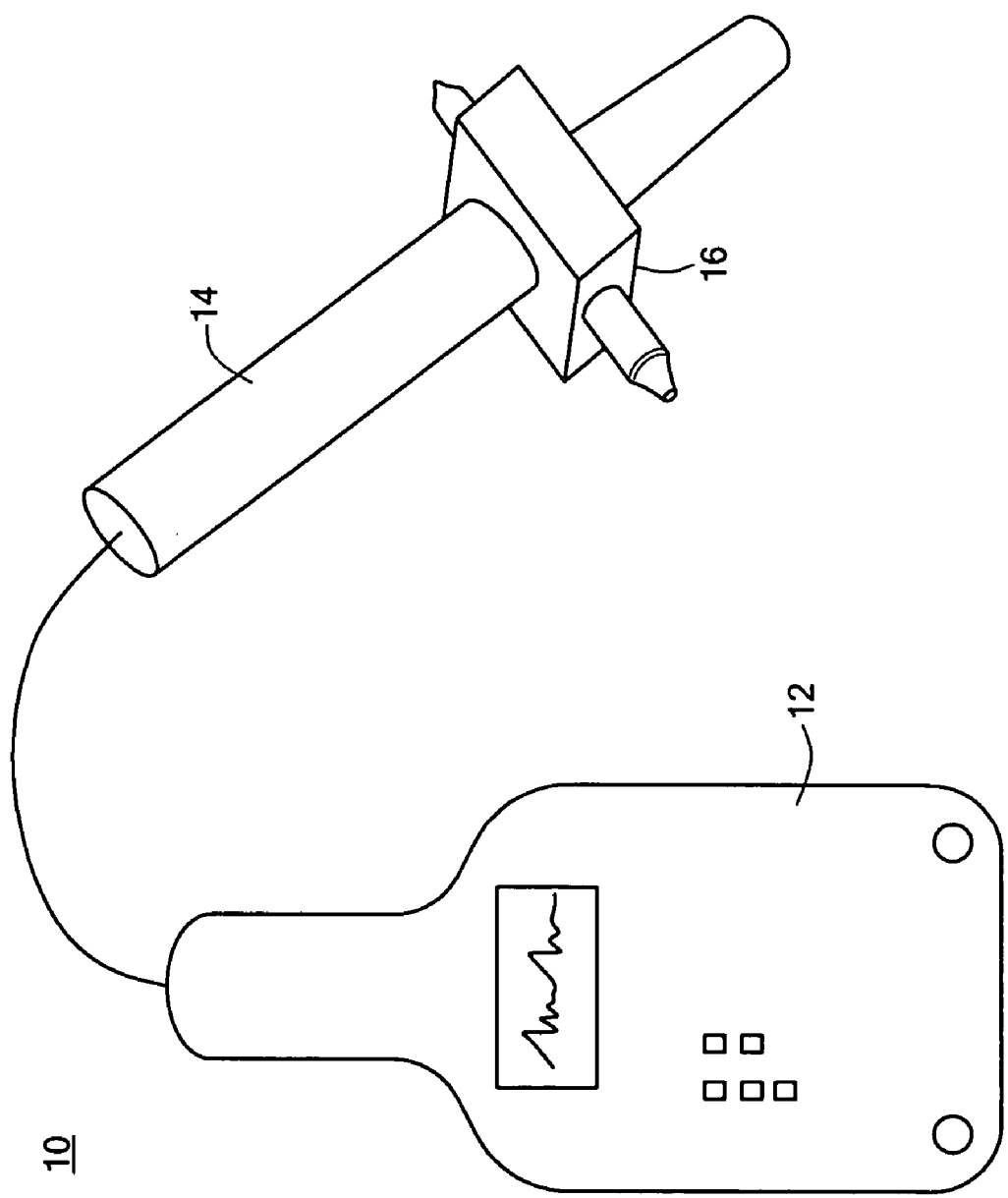
FIG. 1 is a schematic view of a photometer in accordance with the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
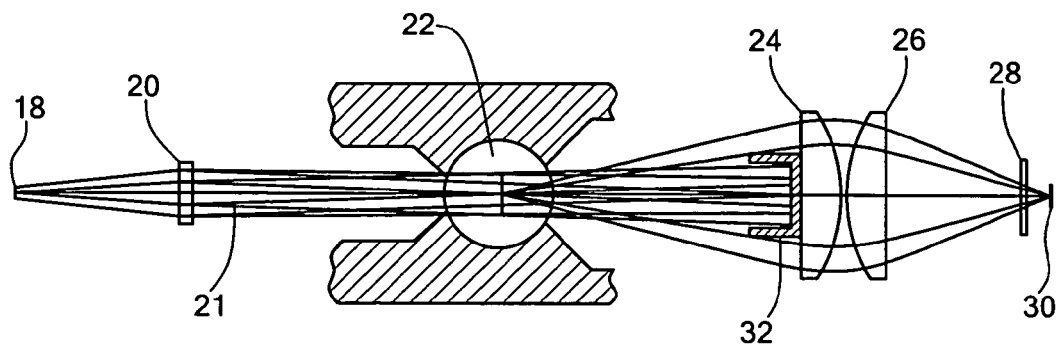
FIG. 2 is a schematic view showing the optical components associated with a typical photometer probe.

Photometer 10, FIG. 1 includes readout unit 12, probe 14, and adapter unit 16. Probe 14 includes a source emitting radiation 18, FIG. 2 collimated by lens 20. The collimated beam 21 passes through a fluid stream of aerosol particles in flow passage 22. Radiation scattered by the particles is directed by lenses 24, 26, and 28 to detector 30. Radiation not scattered by the particles is captured by light trap 32 and is not detected by detector 30. The amount of radiation detected by detector 30 is thus proportional to the concentration of particles in the aerosol stream flowing through passage 22. Read out unit 12, FIG. 1 is responsive to the signal output by detector 30 and may display the concentration of particles in terms of weight per unit volume. As discussed in the background section above, lenses 20 and 24 can be contaminated by the particles of the aerosol stream adversely affecting the accuracy of the photometer. Recalibrating the photometer after each use is a nuisance especially if the photometer is used often. Attempts to purge the lenses with air have been unsuccessful in the case of a low flow rate of the purge air. Too high of a flow rate of purge air dilutes the aerosol stream resulting in erroneous concentration readings.

Figure 3:
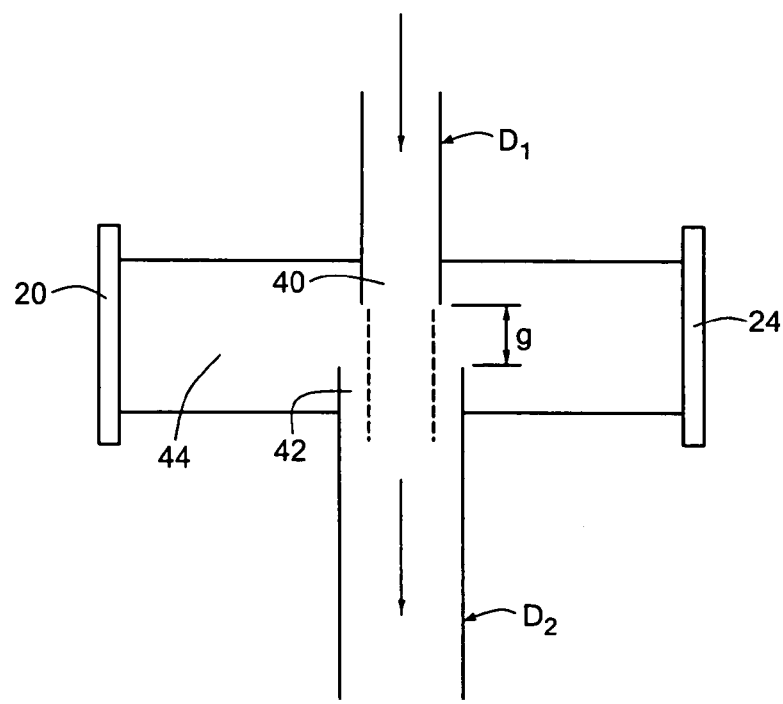
FIG. 3 is a schematic view of an example of a photometer adapter in accordance with the subject invention.

In accordance with the subject invention, fluid (e.g., aerosol) inlet passage 40, FIG. 3 receives aerosol at a specified flow rate and outlet passage 42 is separated from aerosol inlet passage 40 by a gap g. Radiation passage 44 is across gap g and includes lenses 20 and 24.

Contamination of these lenses in accordance with the subject invention is prevented by establishing and maintaining a laminar aerosol flow in aerosol inlet passage 40 and maintaining a laminar flow of the aerosol across gap g. The laminar flow is established and maintained by fixing the Reynolds number ($N_{re}$) for the aerosol stream to be less than 2000.

Achieving a laminar flow depends on the flow rate of the aerosol stream in and the significant dimension of inlet 40. In the case where inlet 40 is in the form of a round conduit, the significant dimension of the inlet is the inside diameter of the conduit. Maintaining a laminar flow across gap g depends on the length of gap g and the significant dimension of outlet 42. In the case of an outlet with the circular cross section, the significant dimension of the outlet is the inside diameter of the outlet conduit.

The Reynolds number for the aerosol stream in inlet 40 is:

$$N_{re} = VD\rho/\mu \quad (1)$$

where V is velocity of the aerosol stream in inlet passage 40, D is the significant dimension of inlet passage 40, $\rho$ is the density of the air, and $\mu$ is the viscosity of the air.

The density and viscosity of the air are typically not variable. But, the significant dimension of inlet passage 40 and the velocity of the aerosol in inlet passage 40 can be varied by design to ensure a Reynolds number of less than 2000 which is indicative of a laminar flow. And, the extent of gap g and the significant dimension of outlet passage 42 can be set by design to maintain a laminar flow of the aerosol across gap g to prevent contamination of lenses 20 and 24.

The velocity of the aerosol stream in inlet passage 40, across gap g, and in outlet passage 42 is typically controlled by a vacuum source, not shown, coupled to outlet passage 42. It is preferred that the significant dimension of the outlet passage 42 be greater than the significant dimension of inlet passage 40. The extent of gap g is preferably slightly larger than the diameter of collimated beam 21, FIG. 2 but as small as possible to maintain a laminar flow across gap g, FIG. 2.

Figure 4:
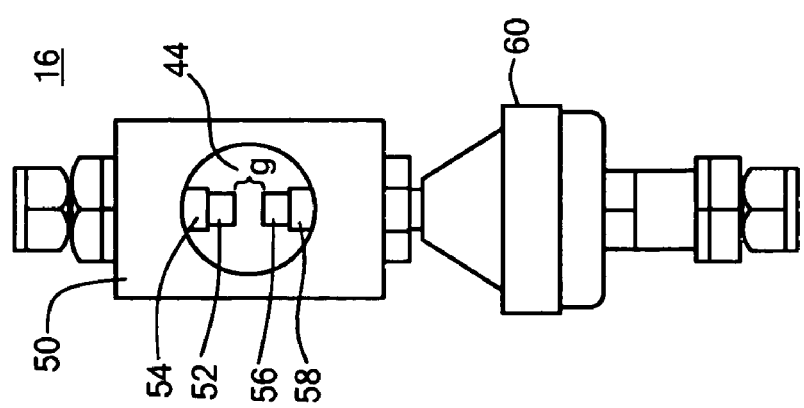
FIG. 4 is a three dimensional schematic view of an embodiment of a particular photometer adapter in accordance with the subject invention.

In one particular example, photometer adaptor 16, FIG. 4 includes main block 50 with radiation passage 44 therethrough. The distal end 52 of aerosol inlet conduit tube 54 is spaced from the distal end 56 of aerosol outlet conduit tube 58 to set gap g. Filter unit 60 may be optionally coupled to outlet tube 58.

Figure 6:
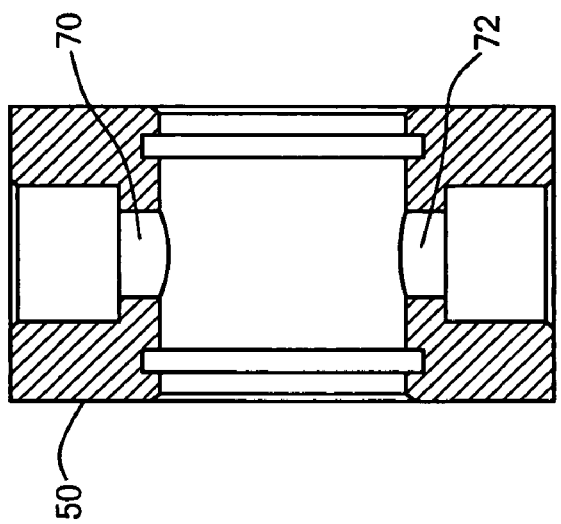
FIG. 6 is a sectional view of the photometer adapter block shown in FIG. 5 taken along line 6-6 of FIG. 5.
Figure 5:
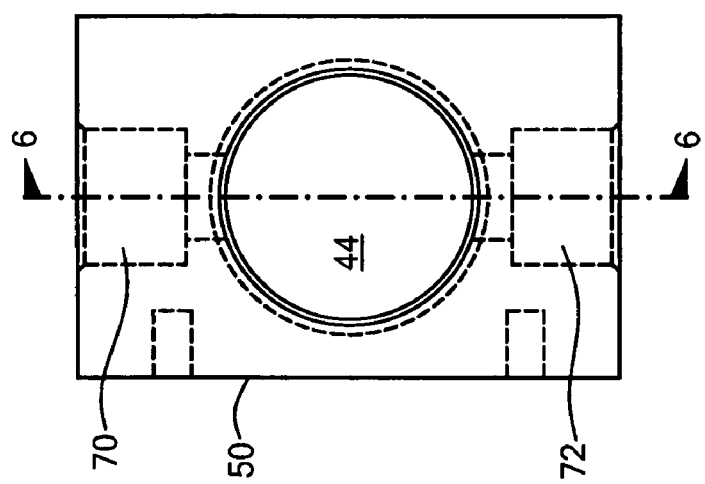
FIG. 5 is a front view of the adapter block for the photometer adapter shown in FIG. 4.
Figure 7:
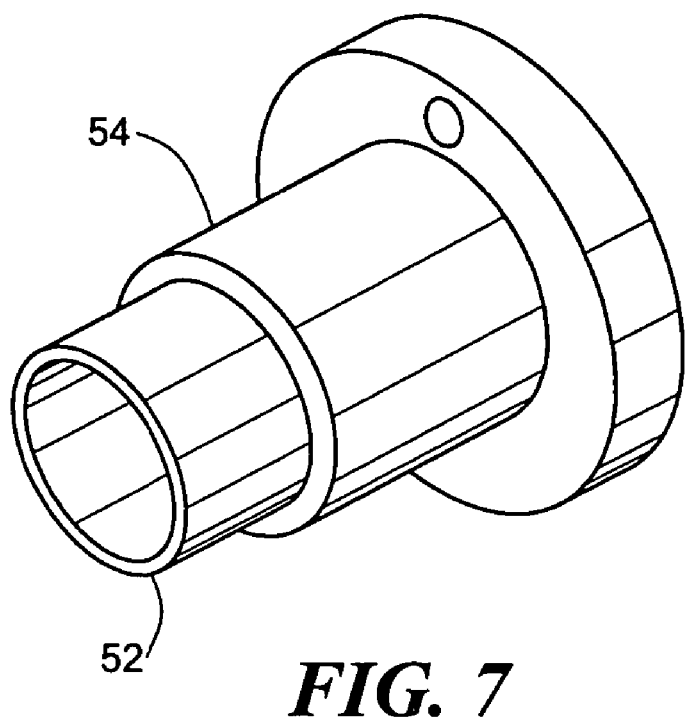
FIG. 7 is a three-dimensional schematic view of the inlet tube component of the adapter shown in FIG. 4.
Figure 8:
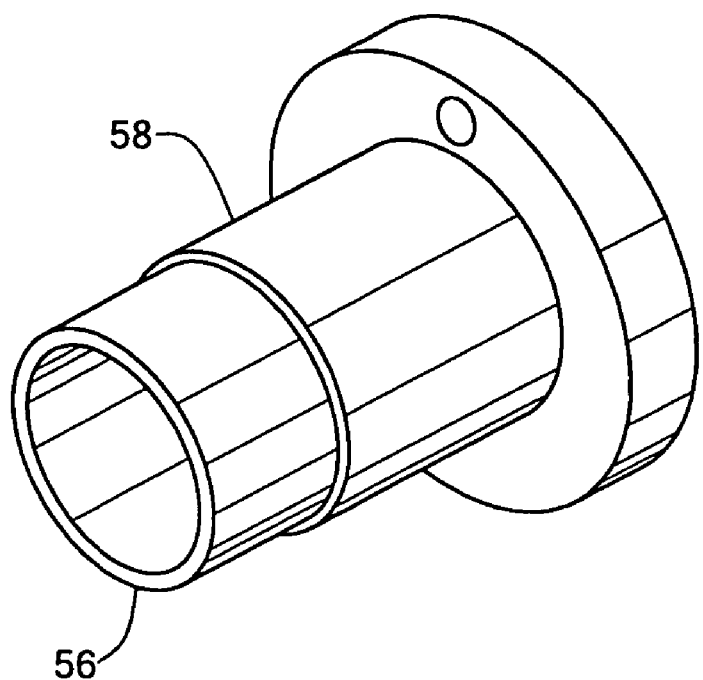
FIG. 8 is a three-dimensional schematic view of the outlet tube portion of the adapter shown in FIG. 4.

Main block 50, FIGS. 5-6 includes radiation passage 44 therethrough and channel 70 which receives inlet tube 54, FIG. 7 having a significant dimension (inside diameter) at distal end 52 of 0.354". Channel 72, FIG. 5 in main block 50 receives outlet tube 58, FIG. 8 which has a significant dimension (inside diameter) at distal end 56 of 0.395". With an air flow rate of 14 l/m, the calculated Reynolds ($N_{re}$) number was less than 2000. Gap g, FIG. 4 was set at 0.355" for a collimated beam diameter of 0.118". The enlarged outlet tube diameter of 0.395" maintained a laminar flow of the aerosol across the gap g.

This example, however, is only one configuration in which a laminar flow of aerosol can be established and maintained across gap g, FIG. 3. The following additional examples are also provided but in no case should the particular embodiments disclosed herein be considered limiting examples. The preferred actual length of the gap is no more than clearance for the optical beam.

| TABLE OF VALUES FOR LAMINAR GAP | | | | | |
|---|---|---|---|---|---|
| Typical Gap | | | | | |
| Flow Rate - 1 pm | 2 | 5 | 10 | 15 | 20 |
| Inlet Diameter - millimeters | 0.9 | 0.9 | 0.9 | 0.9 | 0.9 |
| Reynolds Number | 314 | 786 | 1572 | 2358 | 3143 |
| Outlet Diameter - millimeters | 1 | 1 | 1 | 1 | 1 |
| Reynolds Number | 283 | 707 | 1415 | 2122 | 2829 |
| Maximum Gap | | | | | |
| Flow Rate - 1 pm | 2 | 5 | 10 | 15 | 20 | 40 |
| Inlet Diameter - millimeters | 2.8 | 2.8 | 2.8 | 2.8 | 2.8 | 2.8 |
| Reynolds Number | 101 | 253 | 505 | 758 | 1010 | 2021 |
| Outlet Diameter - millimeters | 3 | 3 | 3 | 3 | 3 | 3 |
| Reynolds Number | 94 | 236 | 472 | 707 | 943 | 1886 |

If Re < 2000 then flow is laminar
If Re > 4000 then flow is turbulent

In one laboratory experiment, a body of Lucite was machined as shown in FIG. 3 to permit the observation of a flow of aerosol from inlet 40 and across the open area g where the radiation beam will pass to the aerosol stream. Microscope slides representing the lens surfaces 20 and 24 were placed on the right and left hand sides of the Lucite block. A series of observational experiments were conducted to determine what happens when the velocity across the optical gap g is in the turbulent versus laminar velocity range. The results were very dramatic. When the flow is turbulent, there was sideways circulation towards both lens surfaces. Subsequent microscopic examination of the microscope slides revealed deposited particulates. When, however, the flow was in the laminar range, the aerosol stream was seen to readily jump the optical gap g with no sideways excursion of the aerosol stream. It was not possible to observe any widening of the aerosol stream at all. Laminar gap g contained the passage of the aerosol with no leakage to lenses 20 and 24. The test aerosol was cigarette smoke which represent the worst case scenario because of its small size (approximately 0.25 µm) and high mobility. Calculations of the Reynolds number were made over the temperature range of −30 to 40° C. to ensure that the flow would not become transitional. Calculations were also made for diffusional particle loss in the inlet tubing 44 to ensure that penetration exceeded 99% over the temperature range and the particle size range of 0.1-10 µm. A seven-day study on ambient air was also conducted. At the end of the study, the slides representing lenses 20 and 24 were examined by a microscope. No deposits were found. Accordingly, the device and method of the subject invention prevents contamination of the radiation passage and the optical components associated therewith (e.g., lenses 20 and 24) without diluting the aerosol stream. As a result, the need for constant recalibration and/or cleaning is reduced if not eliminated.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments including particle monitoring devices other than photometers will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A photometer device comprising:

an inlet passage for receiving a fluid at a specified flow rate;

an outlet passage separated from the inlet passage by a gap;

a radiation passage across the gap; and the flow rate and the significant dimension of the inlet passage set to produce a laminar flow of the fluid and the gap and the significant dimension of the outlet passage set to maintain a laminar flow of the fluid across the gap to prevent contamination of the radiation passage.

2. The device of claim 1 in which the inlet passage significant dimension is less than the outlet passage significant dimension.

3. The device of claim 1 in which the inlet passage is a round conduit and the significant dimension of the inlet passage is the inner diameter of the conduit.

4. The device of claim 1 in which the outlet passage is a round conduit and the significant dimension of the outlet passage is the inner diameter of the conduit.

5. The device of claim 1 in which the photometer device is an adaptor for a photometer probe.

6. The photometer of claim 5 in which the adaptor includes:

a main block with the radiation passage therethrough;

a first channel in the main block transverse to and in communication with the radiation passage for receiving an inlet tube defining the inlet passage; and a second channel in the main block transverse to and in communication with the radiation passage for receiving an outlet tube defining the outlet passage.

7. The device of claim 6 further including a filter unit coupled to the outlet tube.

8. A photometer probe adaptor comprising:

a main block with a radiation passage therethrough;

a fluid inlet conduit in the main block terminating in a distal round inlet end in fluid communication with the radiation passage;

an outlet conduit in the main block terminating in a distal round outlet end in fluid communication with the radiation passage and spaced from the inlet end by a gap within the radiation passage; and the inner diameter of the inlet end less than the inner diameter of the outlet end to produce a laminar flow of the fluid, the inner diameter of the outlet end configured, the gap set, and the flow rate to maintain the laminar flow across the gap to prevent contamination of the radiation passage.

* * * * *